(12) United States Patent
Gallegos

(10) Patent No.: US 9,063,122 B2
(45) Date of Patent: Jun. 23, 2015

(54) BIOMODULATORS FOR TREATMENT OR PREVENTION OF DISEASE

(76) Inventor: Alfredo Gallegos, Mexico (MX)

(*) Notice: Subject to any disclaimer, the term of this patent is extended or adjusted under 35 U.S.C. 154(b) by 670 days.

(21) Appl. No.: 12/581,365

(22) Filed: Oct. 19, 2009

(65) Prior Publication Data

US 2010/0130421 A1 May 27, 2010

Related U.S. Application Data

(60) Provisional application No. 61/106,277, filed on Oct. 17, 2008.

(51) Int. Cl.
| | | |
|---|---|---|
| *A61K 31/40* | (2006.01) | |
| *A61K 31/192* | (2006.01) | |
| *A61K 31/404* | (2006.01) | |
| *G01N 33/50* | (2006.01) | |

(52) U.S. Cl.
CPC ........ *G01N 33/5011* (2013.01); *G01N 2500/10* (2013.01)

(58) Field of Classification Search
None
See application file for complete search history.

(56) References Cited

U.S. PATENT DOCUMENTS

| 5,342,947 A | * | 8/1994 | Lackey et al. | 546/41 |
| 5,605,930 A | * | 2/1997 | Samid | 514/510 |
| 5,783,605 A | * | 7/1998 | Kuo et al. | 514/629 |
| 2004/0162353 A1 | * | 8/2004 | Meyskens et al. | 514/564 |

FOREIGN PATENT DOCUMENTS

| WO | WO2004/093891 | * | 11/2004 |
| WO | WO2005/039546 | * | 5/2005 |
| WO | WO2009/018368 | * | 2/2009 |

OTHER PUBLICATIONS

Ishmael et al (Cancer Investigation, 2003, vol. 21, pp. 542-549).*
Norman et al (Nature, 1965, vol. 206, pp. 477-480).*
Rossiter et al (Bioorganic & Medicinal Chemistry Letters, 2002, vol. 12, pp. 2523-2526).*
Kobayashi et al (Biological and Pharmaceutical Bulletin, 2003, vol. 26, pp. 285-288).*
Pineau et al (Biochemical Pharmacology, 1996, vol. 52, pp. 659-667).*
Bernstein et al (Journal of Neuroscience Research, 1989, vol. 22, pp. 134-143).*

* cited by examiner

*Primary Examiner* — Karen Canella
(74) *Attorney, Agent, or Firm* — Blue Filament Law PLLC; Avery N. Goldstein

(57) ABSTRACT

The invention provides methods and compositions for the treatment or prevention of animal disease whereby the compositions are biomodulators of plant physiological activity. Inventive methods include administration of one or more biomodulators to an animal such as human for the treatment of cell proliferation or differentiation diseases such as cancer.

7 Claims, 4 Drawing Sheets

Descending Legend corresponds to
graph bars from left to right

Myotube Formation in the Presence of TIBA

BIOMODULATORS FOR TREATMENT OR PREVENTION OF DISEASE

CROSS-REFERENCE TO RELATED APPLICATIONS

This application claims priority from U.S. Provisional Application No. 61/106,277 filed Oct. 17, 2008, the entire contents of which are incorporated herein by reference.

FIELD OF THE INVENTION

The present invention relates to compositions including a biomodulator, and methods useful for treating or preventing disease, disorder, or abnormality such as cancer or a neoplastic disorder illustratively by administering a biomodulator compound. The compounds, compositions, and methods of the invention are also useful for inhibiting the growth of a cancer cell or neoplastic cell, treating or preventing a viral infection, or inhibiting the replication and/or infectivity of a virus or bacterial organism. The present invention also has utility to promote multipotent eukaryotic cell growth for the formation of animal stem cells operable for treatment of degenerative disease, neural injury, or other condition for which new cell growth is therapeutic.

BACKGROUND OF THE INVENTION

Significant advances have come rapidly in both our knowledge of, as well as potential uses for, mammalian stem cells of embryonic origin, umbilical cord stem cells, and undifferentiated or pluripotent cells found in all adult human tissues. Around this knowledge a series of new disciplines are gaining acceptance known as regenerative medicine, cell therapy, and cell medicine, among others. With improved understanding there is increasing positive acceptance and confidence in the therapeutic potential of these new and unique treatment strategies by the population. Turning all of these expectations into reality, however, involves long, complex, and expensive interventions.

Cells capable of differentiation and expansion into many or any tissue or organ can be found in adult or embryonic tissue. These "stem cells" are present in both plants and animals. Stem cells can also be created by a process called de-differentiation of adult somatic cells.

All plant cells, if exposed to adequate conditions and specific stimuli, are capable of transforming, into embryonic tissue (formation of callus). Under the right conditions, these cells have the ability to regenerate a complete individual. This attribute of plant cells has been extensively studied since Steward's pioneering efforts at Cornell University in 1958 termed somatic embryogenesis (1).

In June 2007, forty-nine years after the discovery of somatic embryogenesis in plants, S. Chen described a similar process in mammalian cells and named it de-differentiation. Chen observed that cardiac cells (myoblasts) could be induced to de-differentiate into osteoblasts and adipocytes using a purine derivative called "reversine" (3, 4, 5, 6).

Stem cells are also found naturally present in adult tissue. Animal stem cells have the ability to renew themselves or multiply and remain undifferentiated or the stem cells can differentiate into other cell populations. Re-populating hematopoietic stem cells (HSCs) have been identified in mouse bone marrow (14).

Embryonic stem cells were identified in studies by Thomson in 1995 and Shamblot in 1998 (15, 16). Subsequently, Thomson (17) and Gearhart (18) independently described the characteristics and potential attributes of human embryonic stem cells. Numerous reviews and articles on human stem cells have been written (19, 20, and 21), and recently some reports of studies of plant stem cells (22, 23, and 24) have been published.

In plants, meristems or meristematic cells have the ability to regenerate an entire individual (plant) under the influence of auxins/cytokinins using different in vitro, as well as ex vitro, manipulations. The meristems are a group of undifferentiated cells located mainly in the upper (apical) portion of the plant; sometimes they can also be found in roots. These cells known as "plant stem cells" are believed to possess characteristics similar to animal stem cells (26, 27).

Plant stem cells can be quiescent (dormant) at certain times or be activated to divide. The quiescence or activation of stem cells is modulated by shifting balances in the plant hormone signals from their niche. Once the stem cells have divided, the daughter cells receive yet additional plant hormone signals to differentiate, thereby diminishing or abolishing any further cell division.

In plant and tissue culture laboratories, plant stem cells are made to reproduce continually using compounds known as auxins (i.e., 3-indolyl-acetic acid (IAA), 2,4-D dichlorophenoxyacetic acid (2) and cytokinins (kinetin or 6-furfurylaminopurine). Under the influence of auxins, plant tissues form a multicellular balloon-like structure known as a "callus"; the cells of the callus can disperse in liquid growth media. Under proper growth conditions of temperature, asepsis, nutrition, light, and air, the cells will multiply and can be "directed" to differentiate.

Adult plant cells cell can also be made to multiply or differentiate into complete individuals with reproductive organs. Millions of replicas can be easily obtained and transformed into complete individuals (clones) from one or a few undifferentiated plant (meristematic cells). This natural phenomenon is used on a large scale for the production of millions of plant clones and constitutes a procedure of great scientific and economic value, specifically in the citrus (7) and wood (8, 9) industries. Interestingly, development of the pre-embryonic or embryonic tissue (callous formation) is induced by either the cytokinin 6-benzylaminopurine (BAP) or an auxin called 2,4 dichlorophenoxyacetic acid (2,4 D). The differentiation process is optionally induced by increasing the osmotic potential of the growth media. In plant tissue culture, other procedures are also commonly used, such as organogenesis, which involves taking the initial material from a bud or sprout.

The presence of stem cells is now recognized in most eukaryotes, including plants, fungi, alveolates, red algae, moulds, and animals, including humans. Most, if not all, laboratories working with mammalian stem cells use proteins to study growth and differentiation. However, low molecular weight biomodulators are not understood, and represent an innovative approach to solving problems in a new and dynamic biological field.

The term biomodulators describes greater than 150 compounds known that influence the growth and differentiation of plant cells and tissues. Most biomodulators are of low molecular weight. Some effects of biomodulators were described in plants by Bonner (77). An important number of basic cell and tissue functions are present and similar in both plants and animals. However, only recently have we begun to understand their common origin and similarities at the molecular level.

The study of biomodulators has an important practical and economic impact since relevant research is performed with crystalline substances that are easy to handle and store, readily available, and inexpensive, which may balance historical research that has been skewed towards genomics and proteomics (78).

The uncontrolled and exponential growth often found in mammals as cancer, with frequently lethal consequences, does not occur frequently in plants. An exception is some rare, benign, superficial outgrowths of bacterial, fungal or viral origin [for a review, see Bayer et al. (79)]. On the contrary, in plants regulated growth continues until the end of the plant life cycle as seen in the Bristlecone pines of California that are claimed to be 4770 years old. Their continued presence may represent a significant task for their "plant stem cells" (80). Death in plants is mostly observed in response to external factors such as drought, fire, or simply collection or harvest.

Many scientists concerned with mammalian cancer are focusing on "stem cells, cancer, and cancer stem cells" such as Reya (81) and others (82, 83). Mathematical models have been made by Dingli and Michor that suggest that "successful therapy must eradicate cancer stem cells" (84).

The subject application concerns therapeutics operable for cancer treatment that function by modulating, reprogramming, conducting, and maintaining the growth and differentiation of normal and tumor cells by using biomodulators, instead of trying, like prior art cancer therapies do, to kill, destroy, remove, intoxicate, and irradiate all malignant cells.

Despite efforts to fight cancer, many malignant diseases that are of interest in this application continue to present major challenges to clinical oncology. Prostate cancer, for example, is the second most common cause of cancer deaths in men. Current treatment protocols rely primarily on hormonal manipulations. However, in spite of initial high response rates, patients often develop hormone-refractory tumors, leading to rapid disease progression with poor prognosis. Overall, the results of cytotoxic chemotherapy have been disappointing, indicating a long felt need for new approaches to treatment of advanced prostatic cancer. Other diseases resulting from abnormal cell replication, for example metastatic melanomas, brain tumors of glial origin (e.g., astrocytomas), and lung adenocarcinoma, are also highly aggressive malignancies with poor prognosis. The incidence of melanoma and lung adenocarcinoma has been increasing significantly in recent years. Surgical treatments of brain tumors often fail to remove all tumor tissues, resulting in recurrences. Systemic chemotherapy is hindered by blood barriers. Therefore, there is an urgent need for new approaches to the treatment of human malignancies including advanced prostatic, lung, colon, breast and cervical cancers; melanoma; and brain tumors.

SUMMARY OF THE INVENTION

An inventive process is provided for the treatment or prevention of disease whereby a patient at risk of or suffering a disease is administered a therapeutically effective amount of a biomodulator whereby the biomodulator has the ability to influence the growth or differentiation of plant cells. Administration of a biomodulator is preferably in a package that includes a pharmaceutically acceptable excipient that is optionally a physiologically acceptable aqueous or non-aqueous material of a carrier, a diluent, a solvent or a vehicle.

Several routes of administration are operable in the present invention preferably, parenterally, illustratively by intravenous parenteral injection and orally illustratively by solid or liquid dosage form.

The inventive administration of biomodulator is operable for the treatment or prevention of a disease or condition illustratively including malignant or non-malignant conditions. A preferred disease is cancer.

Preferred biomodulators for use in the inventive process illustratively include an auxin, and an antagonist of an auxin.

Also provided is a process for screening mammalian cancer cells for susceptibility to an effective biomodulator that includes exposing a mammalian cancer cell to a first biomodulator that influences growth or differentiation of plant cells; measuring a growth related parameter for the plurality of the cancer cells for inhibition; exposing a second plurality of the cancer cells identical to the first plurality of the cancer cells to a second biomodulator that influences growth or differentiation of plant cells; measuring the growth related parameter for the second plurality of the cancer cells for inhibition; and comparing the growth related parameters for the first biomodulator and the second biomodulator to screen for susceptibility of the cancer cells to one of the first or the second biomodulator. The inventive screening process is either in vitro or in vivo.

Also provided is composition including a purified biomodulator that influences growth or differentiation of plant cells and pharmaceutically acceptable excipient of physiologically acceptable sterile aqueous or non-aqueous material of at least one of a carrier, a diluent, a solvent or a vehicle.

DETAILED DESCRIPTION OF THE PREFERRED EMBODIMENTS

Figure 1:
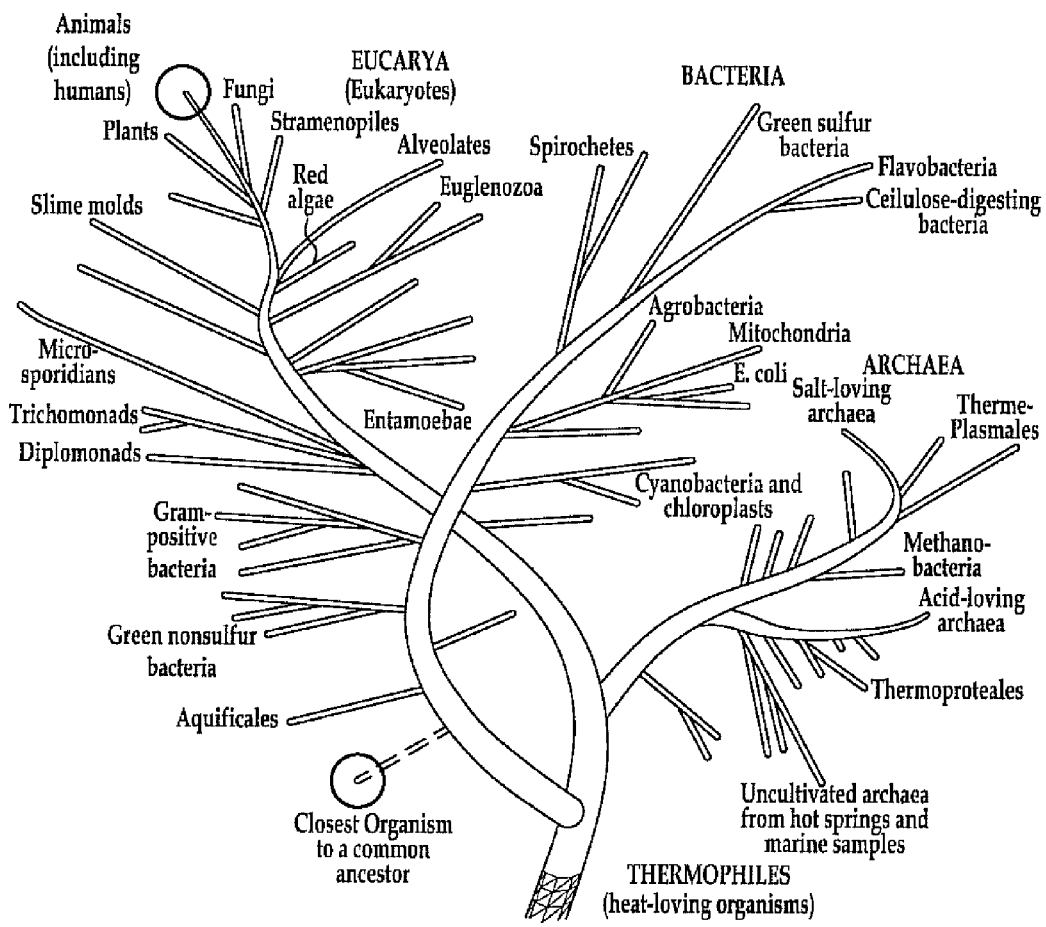
FIG. 1 is a prior art phylum tree of the relation of various organisms.

The present invention involves novel methods for the use of biomodulators and derivative compounds of biomodulators to affect organisms in the domain Eukarya, namely, inducing cell multiplication and cell differentiation, and directing and harmonizing both of these essential cell functions. Thus, the invention has utility as a therapeutic for animal disease or condition, and as control compounds or derivatives thereof for the discovery of therapeutics for animal disease or condition.

Examples of biomodulators operative in the subject invention are illustrated in Table 1.

TABLE 1

| Biomodulators |
|---|
| Auxins |

3-indolyl-acetic acid
2,4-dichlorophenoxyacetic acid
1-naphtalen acetic acid
3-indolebutyric acid
1-naphthylacetic acid
2-naphthyloxyacetic acid
4-chlorophenoxyacetic acid TABLE 1-continued Biomodulators p-chlorophenoxyacetic acid
2-methyl-4-chlorphenoxyacetic acid
2,4,5-trichlorophenoxyacetic acid
3,6-dichloroanisic acid
4-amino-3,5,6-trichloropicolinic acid
2,chloro-3(2,3-dichloro-phenyl)propionitril
Indol-Acetic- Acid-Acetylalanine
acetylglycine
4-chlororesorcinol
Cytokinins 6-furfurylaminopurine
4-hydroxy-3-methyl-trans-2-butenylaminopurine
N6-(2-isopentyl) adenine
6-(4-hidroxy-3-methyl-trans-2-butenyl) aminopurine
ZEATIN RIBOSIDE
6-benzylaminopurine
6-(benzylamino)-9-(2-tetrahydropyranyl)-9H-purine
N-(2-chloro-4-pyridyl)-N'-phenylurea
N-(2,6-dichloro-4-pyridyl)-N'-phenylurea
N-phenyl-N'-1,2,3-thiadiazol-5-ylurea
Gibberillins Acid(1,2,4,10)-2,4,7-trihidroxy-1-methyl-8-methylenegibb-3-ene-1,10 dicarboxylic 1,4-lactone
(1a,2B,4aa,4bB,10B)-2,4,7-Trihydroxy-1-methyl-8-methylenegibb-3-ene-1,10-dicarboxylic acid 1,4-lactone.
Gibberillins Antagonists 2-Chloro-N,N,N-trimethylethanaminium chloride
(2-chloroethyl) trimethylammonium chloride
Butanedioic acid mono(2,2-dimethylhydrazide)
AMO 1618
Carvadan
a-Cyclopropyl-a (4-methoxyphenyl)pyrimidinemethanol
Paclobutrazol
Triadimefon
Tetcyclasis
Tridimenol
Ethylene and Antagonists Ethylene
Aminoethoxyvinylglycine
2,5-NORBORNADIENE NBD
SALICILIC ACID
o-ACETYL-SALICILIC ACID
N-PROPYL GALLATE
3,5-diido-4-hydroxy-benzoic acid
5-methyl-7-chloro-4-ethoxycarbanylmethoxy-2,1,3-benzothiadiazole
(2-chloroethyl)phosphonic acid
Phenolic Compounds 1,3,5-Benzenetriol
PHLORIDZIN
PHLORETIC ACID
CHLOROGENIC ACID
L-TYROSINE
3-(4-hydroxyphenyl)-2-propenoic acid
p-hydroxycinnamic acid
3-(3,4-dihydroxyphenyl)-2-propenoic acid
3,4-dihydroxycinnamic acid
3-(4-Hydroxy-3-methoxyphenyl)-2-propenoic acid
4-hydroxy-3-methoxycinnamic acid
Auxin Antagonists 2,3,5-tri-iodobenzoic acid (TIBA)
3-phenyl-1,2,4-thiadiazol-5-yl)thioacetic acid
N-1-naphthylphthalamic acid
2,4,6-T 2,4,6-trichlorophenoxyacetic acid
p-chlorophenoxyisobutyric acid
5-Methyltryptophan
Cytokinin Antagonists 2,6-DIAMINOPURINE
8-AZAGUANINE
8-AZAADENINE
7-(3-methylbutylamino)3-methyl-H-pyrazolo [4,3-d]-pyrimidine
4-(cyclohexamino)-2-metylthio-H-pyrrolo[2,3]pyrimidine TABLE 1-continued Biomodulators 4-cyclopentylaminopteridine
4-(2-aminoethyl)phenol
a-(aminomethyl)-4-hydroxybenzenemethanol
4-(2-aminoethyl)-1,2-benzenediol
4-(2-aminoethyl)pyrocatechol
Abscisic Acid S-(Z-E)-5-(1-hydroxy-2,6,6-trimethyl-4-oxo-2-cyclohexen-1-yl)-3-methyl-2-4-pentadienoic acid
Steroids BRASSINOLIDE
EPIBRASSINOLIDE
(22S, 23S)24-EPIBRASSINOLIDE
(22S,23S)28-HOMOBRASSINOLIDE
CASTASTERONE
24-EPICASTASTERONE
28-HOMOCASTASTERONE
(22S,23S)24-EPICASTASTERONE
(22S,23S)28-HOMOCASTASTERONE
Other Putrisine
Spermidine
Spermine
DFMA
DMFO
methylglyoxal-bis(guanylhydrazone)
DCHA
CHAP As used herein the term "biomodulator" refers to a molecule derived from or related to molecules derived from a plant. Biomodulators exert an effect on plant cells and are operable to exert an effect on animal cells. Preferably, a biomodulator is a naturally occurring molecule in plants or a synthetic derivative thereof. It is appreciated that a naturally occurring biomodulator is optionally chemically synthesized in vitro, or purified from a source organism, cell, tissue or other material operable for synthesizing one or more biomodulators. A biomodulator is preferably isolated or purified. A biomodulator may be a chemically synthesized analog or derivative of a naturally occurring biomodulator. Analogs or derivatives preferably have substantially the same activity as the naturally occurring biomodulator. Optionally, an analog or derivative has between approximately 10,000 times to 0.001 times the activity of the naturally occurring biomodulator at equivalent concentration. More preferably, an analog or derivative has between 1000 and 0.01 times the activity of the naturally occurring biomodulator at equivalent concentration.

An "isolated" or "purified" biomodulator is substantially free of cellular material or other contaminating proteins from the cell or tissue source from which the biomodulator is derived, or substantially free of chemical precursors or other chemicals when chemically synthesized. The language "substantially free of cellular material" includes preparations of a biomodulator in which the biomodulator is separated from cellular components of the cells from which it is isolated or produced. Thus, a biomodulator that is substantially free of cellular material includes preparations of the biomodulator having less than about 30%, 20%, 10%, 5%, 2.5%, or 1% (by dry weight) of contaminating cellular, synthetic, or precursor material. When the biomodulator is produced by cells in culture, it is also preferably substantially free of culture medium, i.e., culture medium represents less than about 20%, 10%, or 5% of the volume of the biomodulator preparation. When biomodulator is produced by chemical synthesis, it is preferably substantially free of chemical precursors or other chemicals, i.e., it is separated from chemical precursors or other chemicals which are involved in the synthesis of the biomodulator. Accordingly, such preparations of the biomodulator have less than about 30%, 20%, 10%, 5% (by dry weight) of chemical precursors or compounds other than the biomodulator of interest. In a preferred embodiment of the present invention, biomodulators are isolated or purified.

Effects related to or produced by administration of a biomodulator illustratively include: increased or decreased transcription; increased or decreased translation; altered mRNA or protein splicing; altered RNA breakdown; altered protein folding; stimulation or down regulation of one or more intracellular signaling pathways; activation or inhibition of receptor activity; stimulation or inhibition of enzyme activity; increased or decreased lipid synthesis or breakdown; altered cell cycle activity; apoptosis; differentiation; cell growth; angiogenesis; cell proliferation; mobilization or sequestration of intracellular calcium; changes in intracellular pH; changes in osmotic pressure; alteration of intracellular trafficking; cell motility; increased or decreased myoblast formation; maintenance, inhibition, or stimulation of a quiescent state; cell survival; myotube formation; and differential expression of cellular markers.

In one embodiment a biomodulator acts as a signaling molecule or modulates the activity, concentration, synthesis, folding, degradation, or molecular interactions of one or more signaling molecules. Signaling molecules in plants and animals regulate plant growth and differentiation (28, 29). Examples include: (1) systemine, a 200-residue protein, which is a messenger and signaling molecule involved in plant defense processes (30); (2) flageline, which activates the immune system in insects and mammals, as well as plants (31); (3) NOD-40, a polypeptide of 10-13 residues involved in the regulation of plant cell division; (4) PSK, an oligopeptide composed of 4-5 residues that interferes with cell proliferation; (5) Clavata3, a protein composed of 78 residues that is involved in the differentiation of floral meristems; and (6) ZMIGF, which contains 78 residues, and was isolated from maize and found to regulate seed germination. Interestingly, ZMIGF is structurally and immunologically related to human insulin (32, 33). The plant-specific enzyme RuBisCO, which fixes $CO_2$ into carbohydrates in the presence of light, makes up 50% of chloroplast proteins. RuBisCO is believed to be the most abundant protein on earth (see ref. 27, p. 665). Several proteins and signal transduction mechanisms are present in both plants and animals (36).

In one embodiment a biomodulator binds or alters the activity of a receptor. A biomodulator is optionally a ligand for a receptor. A biomodulator is optionally an antagonist of a receptor. A biomodulator illustratively binds to a receptor, prevents or alters the binding of a ligand to a receptor, alters the secondary structure of a receptor, alters the binding of a signaling molecule to a receptor, alters the dissociation constant or other kinetic or binding parameter of a receptor alone or with another molecule, or combinations thereof.

A receptor is preferably a transmembrane receptor. In one embodiment a receptor is a G-protein coupled receptor. Seven transmembrane G-protein-coupled receptors (GPCRs) are commonly used by eukaryotes to sense extracellular signals to switch on cellular responses through the activation of cognate heterotrimeric G-proteins. Plants also use GPCRs to regulate aspects of development and cell signaling. Illustratively, in *Arabidopsis thaliana*, seven different transmembrane receptors have been described and grouped into three families: C-AMP, GCR1, and 7TM. (47) Plkidou-Dymock concluded that those receptors were first present in plants and then appeared in animals. Assmann published a recent review of the knowledge of plant GPCRs (35) the contents of which is incorporated herein by reference.

In one embodiment a biomodulator binds or alters the activity of an ion-channel. In plants as in animals, calcium ions play an essential role in a large number of intra- and extracellular functions. Several super families of calcium-dependent kinases in *Arabidopsis thaliana* are known (37). A biomodulator optionally alters the activity or expression level of a calcium dependent kinase optionally by stimulating the release of intracellular calcium. Calcium or another ion is optionally brought into the intracellular space or removed from the intracellular space by a biomodulator altering the activity of a cell membrane ion channel. Illustratively, a biomodulator binds a calcium, sodium, hydrogen, or other ion channel on the cell exterior surface region. This activates or inactivates the ion channel altering the intracellular ion levels. Optionally, a proton pump is altered by biomodulator interaction which in turn alters the intracellular pH.

In one embodiment a biomodulator binds or alters the activity of a receptor tyrosine kinase. For example, Abscisic acid (ABA), one illustrative biomodulator, is a crucial compound in plants since it controls cell processes associated with changes in temperature, light, draught, and additionally, the dormancy of seeds. ABA also intervenes in the germination process and the control of the opening or closing of stomata in leaves, thus, regulating transpiration during periods of day/night and hot/cold weather. ABA is illustratively isolated from two mammalian species, the rat and the pig. In both species, the molecule is present in most tissues, although it was present at higher concentrations in the brain and liver (38).

In a recent article by Bruzzone, the presence of abscisic acid was measured in human granulocytic series (in concentrations of 0.23+0.09 µmol/mg protein) and a ribose-ADP dependent cytokine was described as its second messenger. ABA is associated with the in vitro stimulation of phagocytosis in white cells, reactivation of oxygen, production of nitrous oxide and chemotaxis, all phenomena that are accompanied by an increase in intracellular calcium (39).

Other effects have been reported to occur in sponges (40) and in hydras, linking the presence of abscisic acid with the stimulation of tissue regeneration, an effect mediated by stem cell stimulation (41).

In an effort to explain the effects of abscisic acid on germination, Fuji (42) identified two specific membrane protein kinases associated with ABA effects. The membrane receptors for abscisic acid and brassinosteroid receptors share common features (43).

In animals, transforming growth factor (TGF-β) acts through the family of transmembrane ser/threonine receptors; these receptors are also found in plants, where they serve as membrane receptors for a series of potent plant polyhydroxylated steroids known as brassinosteroids (47, 48, 49). As such, biomodulators including brassinosteroids and ABA are operable as ligands for tyrosine kinase receptors in the present invention.

In another embodiment, a biomodulator interacts with or alters the activity of a steroid receptor. A steroid receptor is optionally a tyrosine kinase receptor. Over 40 potent brassinosteroids are known in plants. These compounds serve as important biological signals in plants as well as in algae, fungi, and animals.

A review article by Clouse (52) on brassinosteroids states: "Animal steroids have several well-characterized functions in embryonic and post-embryonic development, as well as in the maintenance of homeostasis." Some plants contain the same steroids found in animal systems such as the ecdyesteroids, androgens, estrogens, and corticosteroids as ascertained by Genus (53) and Milanesi (54). The brassinosteroids are the only steroids present in all plants and act as the counterparts to animal steroids. Brassinosteroids in plants function at nano- and micromolar concentrations to regulate important functions such as cell growth and differentiation (55).

Plants have two signaling pathways for steroids that are closely related to brassinosteroid membrane receptors as they are both linked to membrane kinases with similar structures to the TGF-β receptor as well as to receptor tyrosine kinases (56).

Some enzymes present in animals and plants are bioequivalent. For example, the delta 5-alpha steroid dehydrogenase that converts testosterone to dihydro-testosterone is found in a large number of plants. Additionally, when testosterone is incubated in the presence of 5-alpha steroid reductase from plants and human kidney embryonic cells, the testosterone is reduced to dihydrotestosterone (56, 57). As such, in another embodiment a biomodulator interacts with or alters the activity of an enzyme. An enzyme is optionally a transmembrane protein or a soluble protein. It is appreciated that any molecule with enzymatic activity is optionally an enzyme that is subject to modulation by a biomodulator. Illustratively, an RNA molecule with catalytic activity is an enzyme.

A biomodulator is preferably an auxin. Auxins illustratively exert effects by inducing the secretion of hydrogen ions into and through the cell wall in plants. Binding of auxin leads to lipid breakdown and acidification of the wall, increasing its extensibility. Potassium ions are taken into the cell to counteract the electrogenic export of $H^+$ ions (protons) and this has the effect of decreasing the water potential of the cell so that water enters, causing the cell to expand. (2) Auxins also affect RNA metabolism and hence protein synthesis. Without being bound to one mechanism, protein synthesis is hypothetically affected by auxins by their inducing the transcription of specific messenger RNA (mRNA) molecules.

The auxin 2,4-D (2,4-dichlorophenoxyacetic acid) is used primarily for callus induction in suspension cultures, and is replaced by 1-naphtalen acetic acid (NAA) and 3-indolebutyric acid (IBA) when morphogenesis is required. NAA and IBA are favored auxins for inducing shoot growth.

As surprisingly discovered by Applicant, auxins also modulate animal stem cells. Preferably, an auxin biomodulator is used to alter the quiescent state of a stem cell, induce differentiation, or cell growth. As such, auxins are a preferred biomodulator for the treatment of cell growth and differentiation disorders such as cancer.

In another embodiment a biomodulator is a cytokinin. Cytokinins are often used in tissue culture, often together with auxins, to stimulate cell division and control morphogenesis. Another cytokinin, kinetin, was first isolated in 1955 by Miller (58). This compound is found in both plant cells and human cells (59). Its effects are related to the slowing of aging in plants and animals by reducing the formation of free radicals (60, 61). In addition, it protects DNA and prolongs the life span of fibroblasts in human skin (62).

Barciszewski et al. isolated kinetin in human urine (63) while Ishii et al. later demonstrated the induction of granulocytic differentiation in human myeloid leukaemia cells, and apoptosis (64, 65). Similar effects are observed with another growth and differentiation regulator of plant origin known as cotylenine-A (66). (see also ref. 67.)

In another embodiment a biomodulator is a gibberellin. Over 80 different compounds, related by having a chemical structure based on the "gibbane" skeleton, such as those identified from fungi and higher plants and given "GA" numbers are operable examples herein. Preferred gibberellins are: acid (1,2,4,10)-2,4,7-trihydroxy-1-methyl-8-methylenegibb-3-ene-1,10 dicarboxylic 1,4-lactone and gibberellic acid.

Biomodulators serve many functions in plant cells. Standard screening methods for similar or dissimilar activities in animal cells are performed by methods known in the art. Illustratively, a standard cell viability assay following in vitro administration of one or more biomodulators alone, in combination, or in combination with exogenous agents is performed to elucidate phenotypic effects of biomodulator administration. Some auxins of the present invention such as 3-indolyl-acetic acid alter RNA synthesis and thereby affect protein transcription. Standard screening assays such as by protein chip, RNA chip, or other gene expression chip or assay system are optionally employed to characterize downstream effects of biomodulator administration to cells or other in vitro expression systems.

An inventive process includes administering to a patient having or at risk of a disease or condition a therapeutically effective amount of a biomodulator that influences the growth or differentiation of plant cells. It is appreciated that the effect elicited by the biomodulator is preferably due to an activity of the biomodulator similar to the activity of the biomodulator in a plant. Illustratively, an effect is alteration of cell growth. The preferred cell growth activity of a biomodulator in a patient is related to similar cell growth activity in a plant. In a most preferred embodiment the activity of a biomodulator in the subject invention is independent of a toxic effect toward a target cell, tissue, organ, system or subject. Illustratively, U.S. Pat. No. 6,890,948 uses indole-3-acetic acid as a prodrug that is subsequently oxidized by horseradish peroxidase to produce a toxic effect in cells. In contrast a biomodulator in the subject invention preferably functions independent of a toxic effect. A biomodulator preferably functions independent of molecular alterations relative to the modulator as found in plants.

As used herein the term "effective amount" or "therapeutically effective amount" are the concentration, molar administration, or volume of biomodulator operable to produce an effect within a cell, tissue, organ, system, or organism, each from or related to an animal or plant. Standard biomodulator titration assays are optionally employed to decipher an effective amount following identification and characterization of one or more biomodulator effects in an assay system thereby identifying the minimal or maximal effective amount to modulate the system under investigation. For example, the level of ATP within a tumor cell is illustratively altered following biomodulator administration. The level of ATP affects the survivability of the cell. Similarly, a biomodulator alters ion concentration creating a hypo or hypertonic cell leading to rupture and cell death.

Preferably, an effective amount is an amount of a biomodulator that is effective for: treating or preventing cancer or neoplastic disease; inhibiting the growth of a cancer cell or neoplastic cell; treating or preventing a viral infection; or inhibiting the replication or infectivity of a virus or a bacterial organism. Alternatively, an effective amount is the amount necessary to produce elements of differentiation or dedifferentiation of a cell.

Biomodulators alone or in combination with targeting systems can be selectively delivered to a target cell type in an organism. Examples of targeting systems operably herein include lipid delivery, protein delivery such as by antibody ligands, bile acid delivery systems, oligonucleotide delivery systems, or other delivery or targeting systems known in the art. In one embodiment a biomodulator is selectively delivered to a cell by association with an antibody that recognizes an antigen present on a cell surface. An example of antibody targeting of cancer cells for the delivery of a therapeutic agent is described in U.S. Pat. No. 7,183,388, the contents of which are incorporated herein by reference for reagents, methods, materials, protocols, and other relevant teaching therein. In another embodiment a biomodulator is conjugated to a ligand for a specific receptor on a target cell. Examples of ligands and conjugation of a therapeutic are known in the art.

A mechanism of action of a biomodulator in an animal is optionally identical to or dissimilar from its activity in a plant cell. Illustratively, therapeutic and disease state screening is performed by study of overlapping plant/animal mechanisms. The vast majority of animal cell mechanisms and activities are unique to animal cells. However, biomodulators have crossover capacity to affect conserved as well as non-conserved cell activities and mechanisms.

In one embodiment, when administered to a patient, e.g., a mammal for veterinary use or a human for clinical use, the biomodulators are preferably administered in isolated form.

The compounds of the present invention can be administered intravenously, enterally, parenterally, intramuscularly, intranasally, subcutaneously, topically, intravesically, orally, or by any other operable route of administration for either in vivo or in vitro use. The dosage amounts are illustratively based on the effective amounts observed in vitro and in vivo in antitumorigenicity studies. The varied and efficacious utility of the compounds of the present invention is further illustrated by the findings that they may also be administered concomitantly or in combination with other antitumor agents (such as hydroxyurea, 5-azacytidine, 5-aza-2'-deoxycytidine, and suramin); retinoids; hormones; biological response modifiers (such as interferon and hematopoietic growth factors); and conventional chemo- and radiation therapy or various combinations thereof.

An inventive process is provided that uses one or more biomodulators to screen cancer cells for susceptibility to a biomodulator. The inventive process includes exposing a first plurality of cancer cells, illustratively metastatic cancer cells, to a first biomodulator that optionally influences the growth or differentiation of a plant cell and measuring an effect of a biomodulator. Preferably, an effect is a growth related parameter for the plurality of cancers cells to identify the absence or presence of growth inhibition. In one embodiment a cell proliferation assay is used. In another embodiment a cell surface marker for propensity of cell growth is used. The growth or other effect of a biomodulator in a cancer cell is optionally compared to an untreated plurality of cancer cells or non-cancerous cells to determine the presence or absence of biomodulator effect.

In another embodiment a second plurality of cancer cells or non-cancer cells is exposed to a second biomodulator that has an effect in plant cells. The second biomodulator preferably influences the growth or differentiation of plant cells. An effect of the second biomodulator is measured to detect the presence or absence of inhibition. The effect of the second biomodulator is preferably a growth related parameter.

The inventive process preferably includes comparing the related parameters for the first biomodulator with the parameter for the second biomodulator to screen for or otherwise identify susceptibly of the cancer cells to one of the first or second biomodulators.

In a preferred embodiment the inventive process is performed in vitro.

In a preferred embodiment the first biomodulator or the second biomodulator is a control. A control is a molecule or biomodulator that has no recognized or measurable consequence on the effect measured.

The present invention also provides methods of inducing tumor cell differentiation in a host including administering to the host a therapeutically effective amount of biomodulator or a pharmaceutically acceptable derivative thereof.

The present invention also provides methods of preventing the formation of malignancies by administering to a host a prophylactically effective amount of biomodulator or a pharmaceutically acceptable derivative thereof.

The present invention also provides methods of treating malignant conditions, such as prostatic cancer, melanoma, adult and pediatric tumors, illustratively, brain tumors of glial origin, astrocytoma, Kaposi's sarcoma, lung adenocarcinoma and leukemias, as well as hyperplastic lesions, e.g., benign hyperplastic prostate and papillomas by administering a therapeutically effective amount of one or more biomodulators or pharmaceutically acceptable derivatives thereof.

Biomodulators are optionally administered alone or simultaneously with a second biomodulator. Optionally a first biomodulator is administered sequentially with a second biomodulator. Optionally, the number of biomodulators that are administered simultaneously or sequentially is 2, 3, 4, 5, 6, 7, 8, 9, 10 or greater.

The present invention provides methods of treating conditions such as neuroblastoma, promyelocytic leukemia, myelodisplasia, glioma, prostate cancer, breast cancer, melanoma, and non-small cell lung cancer.

A condition effected by a biomodulator is optionally of a non-malignant nature, including, but not limited to, such conditions as non-malignant glioma, benign prostatic hyperplasia, and papillomavirus infection. A related method uses the above steps and further includes the steps of continuously monitoring the subject for rhabdomyolysis-induced myopathy and in the presence of rhabdomyolysis-induced myopathy, administering ubiquinone to the subject.

It is understood that the methods and compositions of this invention can be used to treat animal subjects, including human subjects. As used herein, a subject means: humans, primates, horses, cows, sheep, pigs, goats, dogs, cats, avian species and rodents. The terms subject and patient are used interchangeably herein.

The particular activity of each of the biomodulators of Table 1 and others operable in the subject invention are screened using the assays and models known in the art. Screening assays for activity of molecules are known in the art and regularly practiced. Thus, it is not undue experimentation to determine the amount of biomodulator to administered to elicit an effect.

The present invention provides a further method of treating a neoplastic condition in a subject, including administering a therapeutic amount of hydroxyurea in combination with a therapeutic amount of a biomodulator. This combination therapy method is optionally used to treat neoplastic conditions including prostatic carcinoma.

Methods of making biomodulators are recognized by one of ordinary skill and the art as resulting from general organic chemistry techniques or by purification from a known source.

In a preferred embodiment, biomodulators are used to dedifferentiate cells thereby creating cells that can subsequently differentiate into any of a number of cell types. Essentially by modulating the concentration, timing of dose, and type of biomodulator the invention allows for the formation of undifferentiated cells that can be subsequently manipulated to form a differentiated cell type. Illustratively, a biomodulator is used to dedifferentiate endothelial cells to form cells that are subsequently guided to express characteristics of neural tissue, blood tissue, or lung tissue. More specifically, cells are dedifferentiated to form neuroblastoma cells. Subsequent administration of NeuroD2, one of the neurospecific basic helix-loop-helix transcription factors, leads to subsequent neural cell differentiation. Alternatively, growth factors such as human epidermal growth factor or bovine fibroblast growth factor are used to differentiate cells into a desired neural cell. Concentrations and times of administration of growth factors or differentiation promoting cytokines are known in the art.

Solid dosage forms for oral administration include capsules, tablets, pills, powders, and granules. In solid dosage forms, the therapeutic compound is admixed with at least one inert customary excipient illustratively including sodium citrate or dicalcium phosphate, or a filler illustratively including a starch, lactose, sucrose, glucose, mannitol and silicic acid. Additionally, a binder, humectant, disintegrating agent, solution retarder, absorption accelerator, wetting agent, absorbent or lubricant is operative herein. An oral dosage according to the present invention is optionally formed by mixing isolated or better purified biomodulator that contains minimal quantities of contaminants that can interfere with efficacy with a mixing agent. Mixing agents operative herein are chemically and biologically inert and illustratively include: cellulose acetate phthalate; cellulose acetate trimaletate; hydroxy propyl methylcellulose phthalate; polyvinyl acetate phthalate; ammonio methacrylate copolymers such as those sold under the trademark EUDRAGIT RS and RL; poly acrylic acid and poly acrylate and methacrylate copolymers such as those sold under the trademark EUDRAGIT S and L; polyvinyl acetaldiethylamino acetate; hydroxypropyl methylcellulose acetate succinate; shellac; hydrogels and gel-forming materials, such as carboxyvinyl polymers, sodium alginate, sodium carmellose, calcium carmellose, sodium carboxymethyl starch, poly vinyl alcohol, hydroxyethyl cellulose, methyl cellulose, gelatin, starch; and cellulose based cross-linked polymers such as hydroxypropyl cellulose, hydroxypropyl methylcellulose, polyvinylpyrrolidone, crosslinked starch, microcrystalline cellulose, chitin; aminoacryl-methacrylate copolymer (EUDRAGIT RS-PM, Rohm & Haas); pullulan; collagen; casein; agar; gum arabic; sodium carboxymethyl cellulose; (swellable hydrophilic polymers) poly(hydroxyalkyl methacrylate) (m. wt. about 0.5 k-5,000 k); polyvinylpyrrolidone (MW about 0.10 k-360 k); anionic and cationic hydrogels; copolymers of maleic anhydride, styrene, ethylene, propylene or isobutylene; pectin; polysaccharides such as agar, acacia, karaya, tragacanth, algins and guar; polyacrylamides; POLYOX polyethylene oxides; diesters of polyglucan; crosslinked polyvinyl alcohol; poly N-vinyl-2-pyrrolidone; sodium starch glucolate; hydrophilic polymers such as polysaccharides, methyl cellulose, sodium or calcium carboxymethyl cellulose, hydroxypropyl methyl cellulose, hydroxypropyl cellulose, hydroxyethyl cellulose, nitro cellulose, carboxymethyl cellulose, cellulose ethers, polyethylene oxides, methyl ethyl cellulose, ethylhydroxy ethylcellulose, cellulose acetate, cellulose butyrate, cellulose propionate, gelatin, collagen, starch, maltodextrin, pullulan, polyvinyl pyrrolidone, polyvinyl alcohol, polyvinyl acetate, glycerol fatty acid esters, polyacrylamide, polyacrylic acid; copolymers of methacrylic acid or methacrylic acid; sorbitan esters; natural gums; lecithins; pectin; alginates; ammonia alginate; sodium; calcium; potassium alginates; propylene glycol alginate; agar; and gums such as arabic, araya, locust bean, tragacanth, carrageens, guar, xanthan, scleroglucan; and mixtures, and blends of the aforementioned mixing agents.

Methods involving conventional biological techniques are described herein. Such techniques are generally known in the art and are described in detail in methodology treatises such as Molecular Cloning: A Laboratory Manual, 2nd ed., vol. 1-3, ed. Sambrook et al., Cold Spring Harbor Laboratory Press, Cold Spring Harbor, N.Y., 1989; and Current Protocols in Molecular Biology, ed. Ausubel et al., Greene Publishing and Wiley-Interscience, New York, 1992 (with periodic updates). Immunological methods (e.g., preparation of antigen-specific antibodies, immunoprecipitation, and immunoblotting) are described, e.g., in Current Protocols in Immunology, ed. Coligan et al., John Wiley & Sons, New York, 1991; and Methods of Immunological Analysis, ed. Masseyeff et al., John Wiley & Sons, New York, 1992.

Various aspects of the present invention are illustrated by the following non-limiting examples. The examples are for illustrative purposes and are not a limitation on any practice of the present invention. It will be understood that variations and modifications can be made without departing from the spirit and scope of the invention. While the examples are generally directed to mammalian tissue or cell lines, a person having ordinary skill in the art recognizes that similar techniques and other techniques known in the art readily translate the examples to mammals such as humans. Reagents illustrated herein are commercially available or synthesized by a person of ordinary skill in the art without undue experimentation, and a person of ordinary skill in the art readily understands where such reagents or precursors are obtained. Variations within the concepts of the invention are apparent to those skilled in the art.

EXAMPLES

The herein offered examples, including experiments, provide methods for illustrating, without any implied limitation, the practice of this invention focusing on biomodulators and their derivatives directed to: A. Cancer therapy and prevention; B. Treatment and prevention of AIDS; C. Induction of fetal hemoglobin synthesis in β-chain hemoglobinopathies; D. Use of biomodulators and its derivatives in wound healing; E. Use of biomodulators and its derivatives in treatment of diseases associated with interleukin-6; F. Use of biomodulators and its derivatives in the treatment of AIDS-associated CNS dysfunction; G. Use of biomodulator and its derivatives to enhance immunosurveillance; H. Method of monitoring the dosage level of biomodulator and its derivatives in a patient and/or the patient's response to drugs; I. The activation of a receptor by a biomodulator and its derivatives; J. Use of biomodulator and its derivatives in treatment of cancers having a multiple-drug resistant phenotype; K. Biomodulator and its derivatives in their correlation between potency and lipophilicity; L. Biomodulator and its derivatives in combination with lovastatin for the treatment and prevention of cancers such as malignant gliomas or other CNS tumors; M. Biomodulator and its derivatives in combination with retinoic acid for the treatment and prevention of cancers such as those involving neuroblastoma cells; N. Biomodulator and its derivatives for the treatment and prevention of cancers and other differentiation disorders such as those involving malignant melanoma or other neuroectodermal tumors; O. Biomodulator and its derivatives in combination with hydroxyurea (HU) for the treatment and prevention of cancers such as prostate cancer; P. Biomodulator and its derivatives for the treatment and prevention of cancers involving medulloblastoma and astrocytoma derived cells; Q. Biomodulator and its derivatives in human studies relating to treatments with PA and PB; R. Biomodulator and its derivatives in methods of altering lipid metabolism, including reducing serum triglycerides; and S. Methods of administering biomodulator and its derivatives.

Example 1

Differentiation and Growth of Stem Cells

Reagents: The auxin 2,4-Dichlorophenoxyacetic acid, and auxin antagonist, TIBA (2,3,5-triiodobenzoic acid), are purchased from Sigma-Aldrich (St. Louis, Mo.), After dissolving, these compounds are stored at −20° C. Concentrations used are 0.0001, 0.001, 0.01 and 0.1 µg/ml.

$C_2C_{12}$ muscle stem cells are used. Cells from low-passage frozen stocks are seeded in a 10 cm culture dish. After reaching 60% confluence, cells are passaged into an 8-well chamber slide (BD Biosciences, CA, USA). $C_2C_{12}$ cells are seeded on an 8-well chamber slide ($3.5 \times 10^3$ cells/well). On day 3 after exposure to biomodulator or control, cells are fixed for immunocytochemistry (ICC) of MyoD and Ki67. For MHC and Pax7 immunostaining, cell culture media is replaced from the growth media (GM) to the differentiation media (DM) to induce terminal differentiation at day 5, and then cells are fixed for ICC of MHC and Pax7 at day 8. Media change and compound administration are performed daily.

For ICC, cells are fixed with 4% paraformaldehyde (PFA)/PBS for 20 min at ambient temperature. After being washed with PBS, cells are soaked in 0.1% Triton-X/PBS for 15 min at RT and blocked with 5% normal goat serum (NGS)/PBS to inhibit non-specific binding of antibodies for 60 min at ambient temperature. Primary antibodies are applied, and cells are incubated overnight at 4° C. The primary antibodies are anti-Pax7 mouse monoclonal (Developmental Studies Hybridoma Bank (DSHB), IA), anti-MyoD mouse monoclonal (DSHB), anti-Myosin Heavy Chain mouse monoclonal (MF20; DSHB) and anti-Ki67 rabbit polyclonal (Thermo Fisher Scientific, CA) antibodies.

Cell growth parameters are measured by WST assay. Cell proliferation reagent WST-1 is purchased from Roche (NJ). Assays are performed according to the manufacturer's protocol. Cells are seeded on a 96-well cell culture plate ($1.5 \times 10^3$ cells/well), and absorbance (A450-A690) is measured at day 3.

Figure 2:
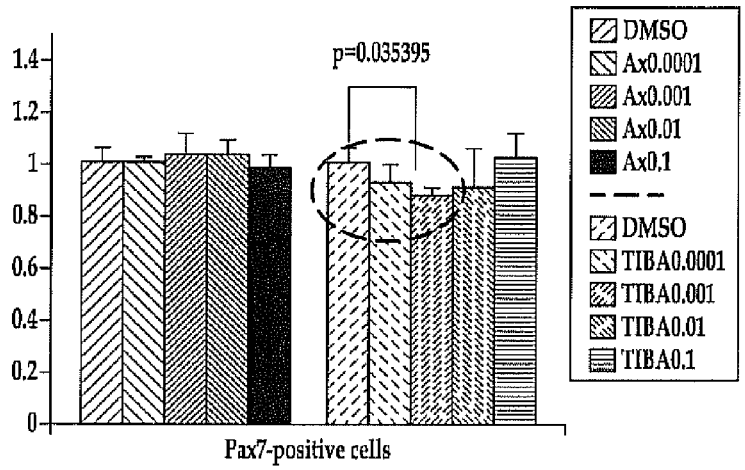
FIG. 2 represents muscle stem cell number in the presence of biomodulators.
Figure 3:
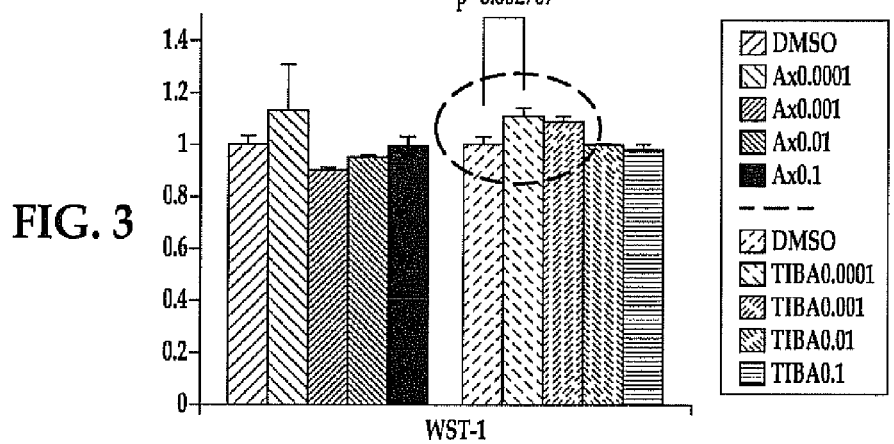
FIG. 3 represents cell growth by WST assay in the presence of biomodulators.

The presence of TIBA at low to mid-level concentrations reduces the number of stem cells in culture. FIG. 2. The trends for auxin are opposite that of TIBA indicating the antagonistic effects of these biomodulators. The reduction in stem cell number correlates with increases in the total number of MyoD negative myoblasts by WST assay. In the WST-1 cell growth assay, low concentration of TIBA (0.001 µg/ml and 0.0001 µg/ml) increases cell number at day 3, which probably represents an increased population size of MyoD negative myoblasts. TIBA also causes a dose-dependent decrease in the number of MyoD positive myoblasts on day 3. This indicates that the presence of TIBA at low to mid concentrations reduces the number of stem cells in a quiescent state and induces differentiation to MyoD negative myoblasts and mature muscle cells.

Figure 4:
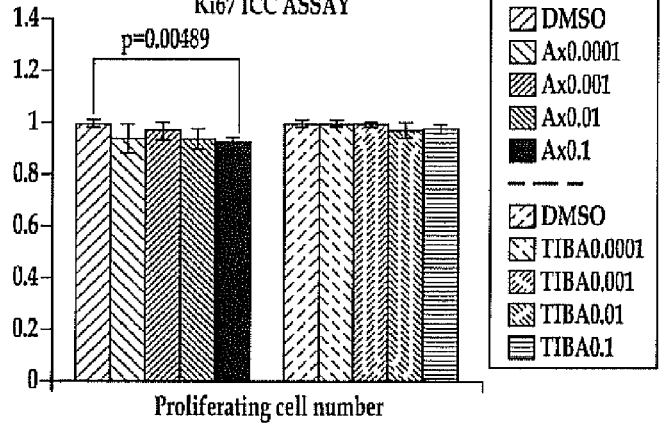
FIG. 4 represents global cell proliferation in the presence of biomodulators.
Figure 5:
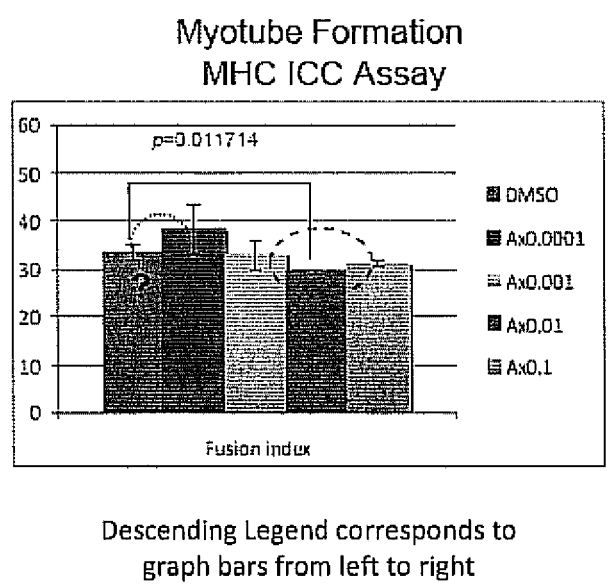
FIG. 5 represents myotube formation in the presence of an auxin at varying concentrations.

Muscle stem cells are also exposed to an auxin biomodulator. In response to differing concentrations of auxin, global cell proliferation is reduced at high Auxin concentrations. FIG. 4. Also, myotube formation is reduced at mid to high auxin concentration (0.01 µg/ml). FIG. 5. It is expected that the increase in myotube formation at the low auxin concentration will be further increased at a more reduced concentration of biomodulator due to the expected differential effects at low and high doses.

Figure 6:
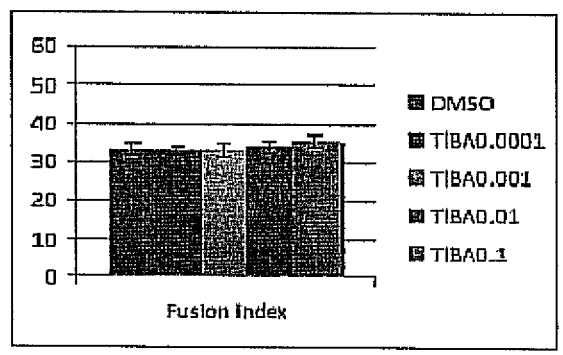
FIG. 6 represents myotube formation in the presence of TIBA at varying concentrations.

Opposite the trend observed for auxin, FIG. 4, the presence of TIBA indicates increased myotube formation with increased concentrations of TIBA further demonstrating the opposite effects of auxin and TIBA. FIG. 6.

Example 2

To demonstrate the effect of biomodulator (3-indolyl-acetic acid) on cell viability, cellular ATP levels are measured before and after treating selected cell lines with Auxin. Selected cell lines include C33A cervical carcinoma cells, Mrc-5 normal lung fibroblasts, PC-3 human prostatic carcinoma cell line, OVCAR-3 human ovarian carcinoma cell line, H460 non-small cell lung cancer cell line, A549 human lung carcinoma cell line, H1299 human non-small cell lung cancer cells, MCF-7 human breast cancer cell line, SW-480 human adenocarcinoma cell line, B16-F1 mouse melanoma cell line (American Type Culture Collection, Manassas, Va., USA), HMEC normal mammary epithelial cells (Clonetics San Diego, Calif., USA) and ADR-RES human breast cancer cell line (NCI, MD, USA), which are cultured in the media recommended by the American Type Culture Collection. The cell lines are plated in 96-well microliter plates (PerkinElmer Life Sciences Inc., Boston, Mass., USA) at a confluency that allows them to reach confluence after 4 days of growth. One day after plating, the cells are treated with various concentrations of biomodulator. Stock solutions of the biomodulator are prepared in dimethyl sulfoxide (Sigma-Aldrich Inc., St. Louis, Mo., USA), diluted in the recommended media and then added to the cells. The total dimethyl sulfoxide on the cells is 1%. After 3 days of incubation the ATP levels in the cells are quantified using a luminescent ViaLight detection system (Bio-Whittaker, MD, USA). The results are plotted relative to untreated control cells, which are set at a value of 100.

Biomodulator has a significantly greater effect on ATP levels in cancer cells than in normal cells. Measurements of ATP levels 72 hours after treatment with 0.5 µM biomodulator indicate that biomodulator is significantly more effective at lowering ATP levels in the cancer cell lines H1299 and C33A compared with the ATP levels in normal cell lines HMEC and MRC-5. These results demonstrate that biomodulator is selectively cytotoxic to cancer cells and is useful for treating or preventing cancer.

To further demonstrate the efficacy of biomodulator as an anti-cancer agent, the effect of various concentrations of biomodulator on cellular ATP levels in ten different cancer cell lines is evaluated. Biomodulator shows greater efficacy in decreasing cellular ATP levels in the cancer cell lines than in the HMEC normal mammary epithelial cell line. These results demonstrate that biomodulator is a selective anti-cancer agent.

Example 3

Biomodulator is administered to 5 different cell lines to induce differentiation in the target cell lines. Standard differentiation markers such as integrin expression, expression of involucrin, secretion of BMP2, Troponin T expression, Stat3 expression, and other known markers of cell differentiation are evaluated following exposure of cells to biomodulator. Expression of BMP2 is analyzed in whole cell lysates by western blot with an anti-BMP2 antibody. Cell culture, lysis, protein detection methods are known and common in the art. In all cell lines the presence of biomodulator induces cell differentiation as measured by the presence of cell specific differentiation markers.

Example 4

Treatment of tumors in mice. A pharmaceutical composition of biomodulator 3-indolyl-acetic acid, or 6-furfurylaminopurine are prepared at 10 mg in 10 ml of physiological saline. 10 mg of a murine colonic tumor, colon 26, is inoculated under the skin of the back of CDF1 mice (day 0). After one week, the tumor is measured to calculate the volume of the tumor and the mice are classified into several groups (each group: n=5). On days 7, 11 and 15, the tumor-inoculated mice are bolusly injected under the skin of their backs and into their tail veins with 1 mg of the biomodulator in a volume of 1 ml. Control and comparative groups of mice are similarly injected with saline. Complete regression of the colonic tumor is determined by palpation. Subjects in which the tumor is ascertained by palpation on the 60th day are deemed to have their tumors cured completely. The injection of either biomodulator alone and in a combination group produces tumor regression.

Various modifications of the present invention, in addition to those shown and described herein, will be apparent to those skilled in the art of the above description. Such modifications are also intended to fall within the scope of the appended claims.

Patents and publications mentioned in the specification are indicative of the levels of those skilled in the art to which the invention pertains. These patents and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The following references are each incorporated herein by reference as if the contents of each reference were fully and explicitly included.

REFERENCES

1. STEWARD F. C., MAPES M. O., SMITH J 1958 GROWTH AND ORGANIZED DEVELOPMENT OF CULTURED CELLS, I GROWTH AND DIVISION OF FREELY SUSPENDED CELLS. AM. J. BOT 45; 639-703.
2. GEORGE E. F. 1993 PLANT PROPAGATION BY TISSUE CULTURE, ED. EXEGETICS LTD. EDINGTON. WILTS BA. ENGLAND. P. 420 and 425.
3. CHEN S. ET AL 2007 REVERSINE INCREASES THE PLASTICITY OF LINEAGE-COMMITED MAMMALIAN CELLS. PNAS. 104 NO 35. 10482-87.
4. CHEN S. ET AL. WORLD INTELLECTUAL PROPERTY ORGANIZATION (WIPO) 2005. (WO/2005/047524) COMPOSITIONS AND METHODS FOR INDUCING CELL DE-DIFFERENTIATION.
5. BEARZI C. ET AL. 2007 HUMAN CARDIAC STEM CELLS. PNAS. 104 NO. 35 14068-73.
6. LERI, A. KAJSTURA, J., ANVERSA P. 2005. CARDIAC STEM CELLS AND MECHANISMS OF MYOCARDIAL REGENERATION PHYSIOL. REV. 85:1373-1416.
7. BAUSHER M., NIEDZ R., HYNDMAN S. 2004. A METHOD OF PRODUCING PLANTS BY SOMATIC EMBRYOGENESIS. U.S. Pat. No. 6,692,963.
8. GUPTA P. K. AND PULLMAN G. S. 1991. METHOD FOR REPRODUCING CONIFEROUS PLANTS BY SOMATIC EMBRIOGENESIS. U.S. Pat. No. 4,957,866.
9. GUPTA P. K. AND PULLMAN G. S 1990 METHOD FOR REPRODUCING CONIFEROUS PLANTS BY SOMATIC EMBRIOGENESIS USING ABSCISIC ACID AND OSMOTIC POTENTIAL VARIATION. U.S. Pat. No. 5,036,007.
10. DICCIONARIO DE LA LENGUA ESPANOLA. 1992 21ST EDITION, P. 344.
11. GILBERT S. F. 2000. DEVELOPMENTAL BIOLOGY. CELL-CELL COMMUNICATIONS IN DEVELOPMENT CHAP. 6 P. 165
12. RYAN C. A., PEARCE G., 2003. SYSTEMINS: A FUNCTIONALLY DEFINED FAMILY OF PEPTIDE SIGNALS THAT REGULATE DEFENSIVE GENES IN SOLANACEAE SPECIES P.N.A.S. 100, P. 14577-14580.
13. RYAN C. A. ET AL. 2002. POLYPEPTIDE HORMONES. THE PLANT CELL 14: S-251-S264.
14. TILL J. E. AND MCCULLOUCH E. A. 1961. A DIRECT MEASUREMENT OF THE RADIATION SENSITIVITY OF NORMAL MOUSE BONE MARROW CELLS. RADIAT. RES. 14; 213-22.
15. THOMSON J. A., KALISHMAN J., GOLOS T. G., DURNING M., HARRIS C. P., AND HEARN J. P. 1995. ISOLATION OF A PRIMATE EMBRYONIC STEM CELL LINE. P.N.A.S. 92, 7844-7848.
16. SHAMBLOT M. J., AXELMAN J., WANG S., BUGG. E. M., LITTLEFIELD J. W. DONOVAN, P. J., BLUMENTHAL P. D., HUGGINS G. R., GEARHAT, J. D. 1998 DERIVATION OF PLURIPOTENT STEM CELLS FROM CULTURED HUMAN PRIMORDIAL GERM CELLS. P.N.A.S. 95, 13726-E 13731.
17. THOMSON, J. A., ET AL. 1998. EMBRIONIC STEM CELL LINES DERIVED FROM HUMAN BLASTOCIST. SCIENCE: 282, 1145-1147.
18. GEARHART, J., 1998. NEW POTENTIAL FOR HUMAN EMBRIONIC STEM CELLS. SCIENCE 282: 1061-1062.
19. STEM CELLS AND THE FUTURE OF REGENERATIVE MEDICINE. NATIONAL RESEARCH COUNCIL 2002, P. 96. ED. NATIONAL ACADEMY PRESS. WASHINGTON D.C.
20. STEM CELLS SCIENTIFIC PROGRESS AND FUTURE RESEARCH DIRECTIONS 2005. UNIVERSITY PRESS OF THE PACIFIC. HONOLULU, HAWAII, P. 106.
21. MAYANI H. AND WAGNER J. E. 2003. BIOLOGY AND CLINICAL APPLICATIONS OF HEMATOPOYETIC STEM CELLS. ARCHIVES OF MEDICAL RESEARCH, VOL. 34, NO. 6, NOV-DIC. P. 162.
22. SABLOWSKY R. 2004. PLANT AND ANIMAL STEM CELLS: CONCEPTUALLY SIMILAR, MOLECULARLY DISTINCT ?. TRENDS CELL BIOL. NOV; 14 (11): 605-11.
23. BEN SCHERES. 2005. STEM CELLS: A PLANT BIOLOGY PERSPECTIVE. CELL. VOLUME 122, ISSUE 4, PAGES 499-504.
24. TUCKER W. R. AND LAUX T. 2007. CONNECTING THE PATHS IN PLANT STEM CELL REGULATION. TRENDS IN CELL BIOLOGY. VOLUME 17, ISSUE 8, PAGES: 403-410.
25. HURTADO D., MERINO M., 2001 CULTIVO DE TEJIDOS VEGETALES ED. TRIILLAS, P. 133.
26. GILBERT S. F. 2000. DEVELOPMENTAL BIOLOGY. 6TH ED. SINAUER ASSOC. MASS. USA. P. 635.
27. LODISH H., BERK A., ZIPURSKY, S. L., NATSUDAIRA, P., BALTIMOR, D., DARNELL, J. 2000 MOLECULAR CELL BIOLOGY. 4TH EDITION. ED. W.H. FREEMAN AND CO. P. 852.
28. RYAN C. A. AND PEARCE G. 2001. POLYPEPTIDE HORMONES. PLANT PHYSIOL. VOL. 125, PP. 65-68.

29. FRANSSEN H. J. AND BISSELING T. 2001. PEPTIDE SIGNALING IN PLANTS. PNAS. VOL. 98, NO. 23, 12855-12856.
30. RYAN C. A. AND PEARCE G. 2003. SYSTEMINS: A FUNCTIONALLY DEFINED FAMILY OF PEPTIDE SIGNALS THAT REGULATE DEFENSIVE GENES IN SOLANACEAE SPECIES. PNAS. VOL. 100, SUPPL. 2, 14577-14580.
31. HAYASHI, K. D. SMITH, A. OZINSKY, T. R. HAWN, E. C. YI, D. R. GOODLETT, J. K. ENG, S. AKIRA, D. M. UNDERHILL, Y. A., 2001. "THE INNATE IMMUNE RESPONSE TO BACTERIAL FLAGELIN IS MEDIATED BY TOLL-LI-KE RECEPTOR 5", NATURE 410, 1099-1103.
32. GARCIA F. C. AGUILAR R., BRIONES E., SANCHEZ DE JIMENEZ, E., 2001. A MAIZE INSULINE-LIKE GROWTH FACTOR SIGNALS TO A TRANSDUCTION PATHWAY THAT REGULATES PROTEIN SYNTHESIS IN MAIZE. BIOCHEM. J., 358, 95-100.
33. SANCHEZ DE JIMENEZ E., BELTRAN-PENA E., ORTIZ-LOPEZ A. 1999 INSULIN-STIMULATED RIBOSOMAL PROTEIN SYNTHESIS IN MAIZE EMBRIONIC AXES DURING GERMINATION. PHYSIOLO PLANT 105, 148-155.
34. PLKIDOU-DYMOCK S., DYMOCK D., HOOLEY R. 1998. A HIGHER PLANT SEVEN TRANS MEMBRANE RECEPTOR THAT INFLUENCES SENSITIVITY TO CYTOKININS. CURRENT BIOLOGY VOL. 6, NO. 6 PP 315-324.
35. ASSMANN S. M., 2005. G PROTEINS GO GREEN: A PLANT G PROTEIN SIGNALING FAQ SHEET. SCIENCE, 310, 5745.71-73.
36. NAGATA T. ET AL. 2004. COMPARATIVE ANALYSIS OF PLANT AND ANIMAL CALCIUM SIGNAL TRANSDUCCION ELEMENT USING LANT FULL-LENGTH coda DATA. MOLECULAR BIOLOGY AND EVOLUTION VOL. 21. (10) 1855-1870.
37. HRABAK. E. ET AL. 2003. THE ARABIDOPSIS CDPK-SNRK SUPERFAMILY OF PROTEIN KINASES. PLANT PHYSIOLOGY 132: 666-680.
38. M. TH, LE PAGE-DEGIVRY J. N., BIDARD E., ROUVIER C., BULARD M LAZDUNKI 1986. PRESENCE OF ABSCISIC ACID A PHYTOHORMONE IN THE MAMMALIAN BRAIN. PNAS. 83; 1155-1158.
39. BRUZZONE S. ET AL. 2007. ABSCISIC ACID IS AN ENDOGENOUS CYTOKINE IN HUMAN GRANULOCYTES WITH CYCLIC ADP-RIBOSE AS SECOND MESSENGER. P.N.A.S. VOL. 104, NO 14, 5759-64.
40. ZOCCHI. E. ET AL. 2001. THE TEMPERATURE-SIGNALING CASCADE IN SPONGES INVOLVES A HEAT-GATED CATION CHANNEL, ABSCISIC ACID, AND CYCLYC ADP-RIBOSE. P.N.A.S. VOL. 98, NO. 26, 1485-64.
41. PUCE S. ET AL. 2004. ABSCISIC ACID SIGNALING THROUGH CYCLIC ADP-RIBOSE IN HYDROID REGENERATION. J. BIO. CHEM. VOL. 279, NO. 38, 39783-39788.
42. FUJI H., VERSIUES P E., ZHU J K. 2007. IDENTIFICATION OF TWO PROTEIN KINASES REQUIRED FOR ABSCISIC ACID REGULATION OF SEED GERMINATION, ROOT GROWTH AND GENE EXPRESSION IN ARABIDOPSIS. PLANT CELL. VOL. 19. NO. 2, 485-94.
43. OSAKABE Y., MURUYAMA K., SEKI M., SATU M., SHINOZAKI K. 2005 LEUCINE RICH REPEAT RECEPTOR-LIKE KINASE 1 IS A KEY MEMBRANE BOUND REGULATOR OF ABSCISIC ACID EARLY SIGNALING IN ARABIDOPSIS. PLANT CELL 4; 1105-1109.
44. CARPI. A., DI MAIRA G., VEDOVATO M., ROSSI V., NACCARI T., FLORIDUZ, M., FILIPPINI F., 2002 COMPARATIVE PROTEOME BIOINFORMATICS; IDENTIFICATION OF A WHOLE COMPLEMENT OF PUTATIVE PROTEIN TYROSINE KINASE IN THE MODEL FLOWERING PLANT ARABIDOPSIS THALIANA. PROTEOMICS NOV. 2 (11) 1494-503.
45. GUILLEN. G., ET AL. 1999. PROFILIN IN PHASEUS VULGARIS IS ENCODED BY TWO GENES (ONLY ONE EXPRESSED IN ROOT NODULES) BUT MULTIPLE ISOFORMS ARE GENERATED IN VIVO BY PHOSPHORYLATION ON TYROSINE RESIDUES. PLANT J. 19 (5) 497-508.
46. LI. XIAOHOUNG, LI. HIS-PING, AMSLER K., HYINK D, WILSON P. D., BURROW C, R., PRKY, 2002. A PHYLOGENETICALLY AND FUNCTIONALLY DISTINCT c AMP-DEPENDENT PROTEIN KINASE, ACTIVATES RENAL EPITHELIAL CELL MIGRATION A MORPHOGENESIS. P. N. A. S. VOL. 99, NO. 14 P. 9260-65.
47. JIANG. J., CLOUSE S. D. 2001. EXPRESSION OF A PLANT GENE WITH SEQUENCE SIMILARITY TO ANIMAL TGF-B RECEPTOR INTERACTING PROTEIN IS REGULATED BY BRASSINOSTEROIDS AND REQUIRED FOR NORMAL PLANT DEVELOPMENT. PLANT J. 26; 1; 35-46.
48. CLOUSE. S. D. 2002 BRASSINOSTEROIDS SIGNAL TRANSDUCTION: CLARIFYING THE PATHWAY FROM LIGAND PERCEPTION TO GENE EXPRESSION. MOLECULAR CELL, VOL. 10, PP. 973-982.
49, LI J., CHORY J. 1997. A PUTATIVE LEUCINE-RICH-REPEAT RECEPTOR KINASE INVOLVED IN BRASSINOSTEROID SIGNAL TRANSDUCTION CELL. VOL. 90. 929-38.
50. RENSING A. S., ET AL. 2008. THE PHYSCOMITRELLA GENOME REVEALS EVOLUTIONARY INSIGHTS INTO THE CONQUEST OF LAND BY PLANTS. SCIENCE. VOL. 319, PP. 64-69.
51. SOUTHWOOD R. 2003. THE STORY OF LIFE. OXFORD UNIVERSITY PRESS. P. 82.
52. CLOUSE S., SASSE, J. 1998. BRASSINOSTEROIDS: ESSENTIAL REGULATORS OF PLANT GROWTH AND DEVELOPMENT. ANNU. REV. PLANT. PHYSIOL. PLANT. MOL. BIOL. 49; 427-451.
53. GEUNS J. M. C., 1978 STEROID HORMONES AND PLANT GROWTH AND DEVELOPMENT PHYTOCHEMISTRY. 17, 1-14.
54. MILANESI L., MONJE P., BOLAND R. PRESENCE OF ESTROGENS AND BESTROGEN RECEPTOR-LIKE PROTEINS IN SOLANUM GLAUCOPHYLLUM 2001 BIOCHEM. BIOPHY RES COMMM. 289; 1175-79.
55. FRIEDRICHSEN D. AND CHORY J. 2001. STEROID SIGNALING IN PLANTS: FROM THE CELL SURFACE TO THE NUCLEUS. BIOESSSAYS 23, P. 1028-1036.
56. LI J. BISWAS, M. G., CHAO A., RUSSELL, D. W., AND CHORY, J. 1997. CONSERVATION OF FUNCTION BETWEEN MAMMALIAN AND PLANT STEROID 5-ALPHA REDUCTASES. P.N.A.S. 94: 3554-3559.
57. ROSATI F., DANZA G., GUARNA A., CINI N., RACCHI M. L., SERIO M. 2003 NEW EVIDENCE OF SIMILARITY BETWEEN HUMAN AND PLANT STEROID METABOLISM. ENDOCRINOLOGY 220-9.

58. MILLER C. O., SKOO F., VON SALTZA, M. H., STRONG M. 1955 KINETIN, A CELL DIVISION FACTOR FROM DEOXYRIBONUCLEIC ACID. J. AM. CH. SOC. 77 1329-1334.
59. BARCISZEWSKI J., SIBOSKA G. G., CLARK B. F. C., RATTAN 2000 CYTOKININ FORMATION BY OXIDATIVE METABOLISM J. PLANT PHYSIOLOGY 157; 587-58.
60. LESHEY. Y. 1988 PLANT SENESCENCE PROCESSES AND FREE RADICALS. FREE RADICAL BIOL MED. 5; 39-49.
61. RATTAN S. I. S., 2002 N-6 FURFURYLADENINE (KINETIN) AS A POTENTIAL ANTI-AGING MOLECULE. J. ANTIAGING. MED 5; 113-116.
62. RATTAN S. I. S., CLARK B. F. C., 1994 KINETIN DELAYS THE ONSET OF AGING CHARACTERISTICS IN HUMAN FIBROBLASTS. BIOCHEM. BIOPHYS. RES. COMMM. 201; 665-672.
63. BARCISZEWSKI J., MIELCAREK M., STOBIECKI M., SIBOSKA G., CLARK B. F. 2000 IDENTIFICATION OF 6-FURFORYADENINE (KINETIN) 1N HUMAN URINE. BIOCHEM. BIOPHYS. RES. COMM. 279; 69-73.
64. ISHII Y., HORI Y., SAKAI S., HONMA Y. 2002 CONTROL OF DIFFERENTIATION AND APOPTOSIS OF HUMAN MYELOID LEUKEMIA CELLS BY CYTOKININS AND CYTOKININ NUCLEOSIDES, PLANT REDIFFERENTIATION-INDUCING HORMONES CELL GROWTH & DIFFERENTIATION 13; 19-26.
65. HONMA Y., ISHII Y. 2002. DIFFERENTIATION OF HUMAN MYELOID LEUKEMIA CELLS BY PLANT REDIFFERENTIATION-INDUCING HORMONES. LEUKEMIA & LYMPHOMA 43; 1729-1735.
66. YAMADA K., HONMA A., ASAHI K., SASSA T., HMO K., YOMOYASU S., 2001. DIFFERENTIATION OF HUMAN ACUTE MYELOID LEUKEMIA CELLS IN PRIMARY CULTURE IN RESPONSE TO COTYLENIN A. A PLANT GROWTH REGULATOR. BRITISH J. OF HAEMATOLOGY. VOL. 114; 4; 814-821.
67. HEBERER G. KIEBER J. J 2002. CYTOKININS. NEW INSIGHTS INTO A CLASSIC PHYTOHORMONE. PLANT. PHYSIOLOGY 128: 354-362.
68. WOESE C. R. 19650N THE EVOLUTION OF THE GENETIC CODE. P.N.A.S. 54; 1546-1552.
69. WHEELIS M. L., KANDLER O., WOESE C. R., 1992 ON THE NATURE OF GLOBAL CLASSIFICATION. PNAS. 89 2930-94.
70. WOESE C. R. 20020N THE EVOLUTION OF CELLS. PNAS. 99, 8742-47.
71. BULT, C. J., WHITE, O., OLSEN, G. J., ZHOU, L., FLEISCHMANN, R. D., SUTTON, G. G., BLAKE, J. A., FITZGERALD, L. M., CLAYTON, R. A., GOCAYNE, J. D., KERLAVAGE, A. R., DOUGHERTY, B. A., TOMB, J. F., ADAMS, M. D., REICH, C. I., OVERBEEK, R., KIRKNESS, E. F., WEINSTOCK, K. G., MERRICK, J. M., GLODEK, A., SCOTT, J. L., GEOGHAGEN, S. M., WEIDMAN, J. F., FUHRMANN, J. L., NGUYEN, D., UTTERBACK, T. R., KELLEY, J. M., PETERSON, J. D., SADOW, P. W., HANNA, M. C., COTTON, M. D., ROBERTS, K. M. HURST, M. A., KAINE, B. P., BORODOVSKY, M., KLENK, H. P., FRASER, C. M., SMITH, H. O., WOESE, C. R. AND VENTER, J. C. 1996 "COMPLETE GENOME SEQUENCE OF THE METHANOGENIC ARCHAEON, METHANOCOCCUS JANNASCHII" SCIENCE 372, 1058-73.
72. ARREDONDO-PETER R., ESCAMILLA J. E. 1991 A CONSENSUS OF PLANT HEMOGLOBINS. PLANT MOL. BIOL. REP. 9.195-707.
73. VINAGRADOV S. N., HOOGEWIJS D., BAILLY X. ARREDONDO-PETER R. GOGH J. DE WILDE S. MOENS L. V N FLETERE J. 2006 A PHYLOGENOMIC PROFILE OF GLOBINS BASED ON A SURVEY OF GENOMES FROM THE 3 KINGDOMS OF LIFE. BMC. EVOL. BIOL. 6, 31-47.
74. WENDEHENNE D., PUGIN A., KESSING D. F., DURNER J., 2001 NITRIC OXIDE: COMPARATIVE SYNTHESIS ANS SIGNALLING IN ANIMALS AND PLANT CELLS. TRENDS PLNT SCI. 4; 177-183.
75. BELIGNI M. V., LAMATTINA L. 2001 NITRIC OXIDE IN PLANTS: THE HISTORY IS JUST BEGINNING. PLANT, CELL & ENVIRONMENT 24; 267-78.
76. THE MERCK INDEX. 12TH EDITION 1990, P 2208 AND 4668.
77. BONNER D. M., HAAGEN-SMITH A. L. 1939 LEAF GROWTH FACTORS II-THE ACTIVITY OF PURE SUBSTANCES IN LEAF GROWTH. PNAS. 25.184-188.
78. SPRING. D. H. 2005. CHEMICAL GENETICS TO CHEMICAL GENOMICS: SMALL MOLECULES OFFER BIG INSIGHTS. CHEM. SOC. REV. 34: 472-482.
79. BAYER M H. KAISER M E., MICOZZI M S., 1994. ABNORMAL GROWTH PROCESSES IN PLANTS AND ANIMALS: A COMPARISON. IN VIVO 1., 3-15.
80. THE CHAMPION TREE PROJECT INTERNATIONAL-VISIT—WWW.CHAMPIONTREEPROJECT.ORG.
81. REYA T., MORRISON S. J., CLARKE M. F., WEISSMAN I. L., 2001 STEM CELLS, CANCER, AND CANCER STEM CELLS. NATURE 414, 105-111.
82. DICK J. E. 2003. BREAST CANCER STEM CELLS REVEALED PNAS.; 100. 3547-49.
83. WANG ET AL. 2007 IDENTIFICATION OF CANCER STEM CELL-LIKE SIDE POPULATION CELLS IN HUMAN NASOPHARYNGEAL CARCINOMA CELL LINE. CANCER RESEARCH 67, 3716-24.
84. DINGLI D., MICHOR F., 2006 SUCCESSFUL THERAPY MUST ERADICATE CANCER STEM CELLS. STEM CELLS 24, 2603-10.
85. FOLKES L. K., WARDMAN P. 2003 ENHANCING THE EFFICACY OF PHOTODYNAMIC CANCER THERAPY BY RADICALS FROM PLANT AUXIN (INDOL-3-ACETIC ACID). CANCER RESEARCH 63, 776.
86. WARDMAN P. 2001. USE OF INDOL-3-ACETIC ACID IN MEDICINE. U.S. Pat. No. 6,890,948.
87. FOLKES L. K., WARDMAN P. 2001. OXIDATIVE ACTIVATION OF INDOL-3-ACETIC ACID TO CYTOTOXIC SPECIES A-POTENTIAL NEW ROLE FOR PLANT AUXINS IN CANCER THERAPY. BIOCHEMICAL PHARMACOLOGY. 61.129-136.
88. FOLKS L. K. ROSSITER S., WARDMAN P., 2002 REACTIVITY TOWARDS THIOLS AND CYTOTOXICITY OF 3-METHLYNE-2-OXINDOLES, CYTOTOXINS FROM INDOLE-3-ACETIC ACIDS, ON ACTIVATION BY PEROXIDASES. CHEM. RES TOXICOL. 15; 877-882.

The invention claimed is:

1. A process for treating a non-malignant glioma or benign prostatic hyperplasia comprising: administering to a patient suffering from the disease or the condition a therapeutically effective amount of a biomodulator in the form of an auxin consisting essentially of indole-3-acetic acid that influences growth or differentiation of plant cells; and wherein said biomodulator functions independent of molecular alterations relative to said auxin as found in plants.

2. The process of claim 1 wherein said biomodulator is purified and delivered in a pharmaceutically acceptable excipient.

3. The process of claim 2 wherein said excipient is physiologically acceptable sterile aqueous or non-aqueous material of a carrier, a diluent, a solvent or a vehicle.

4. The process of claim 1 wherein administration is parenterally.

5. The process of claim 4 wherein administration is by intravenous parenteral injection.

6. The process of claim 1 wherein administration is orally.

7. The process of claim 6 wherein administration is by way of a solid dosage form.

\* \* \* \* \*